United States Patent
Proksa et al.

(10) Patent No.: US 8,653,471 B2
(45) Date of Patent: Feb. 18, 2014

(54) SPECTRAL IMAGING

(75) Inventors: Roland Proksa, Hamburg (DE);
Christoph Herrmann, Aachen (DE);
Walter Ruetten, Linnich (DE)

(73) Assignee: Koninklijke Philips N. V., Eindhoven (NL)

( * ) Notice: Subject to any disclaimer, the term of this patent is extended or adjusted under 35 U.S.C. 154(b) by 189 days.

(21) Appl. No.: 13/255,518

(22) PCT Filed: Feb. 18, 2010

(86) PCT No.: PCT/IB2010/050729
§ 371 (c)(1),
(2), (4) Date: Sep. 9, 2011

(87) PCT Pub. No.: WO2010/109355
PCT Pub. Date: Sep. 30, 2010

(65) Prior Publication Data
US 2012/0001084 A1  Jan. 5, 2012

Related U.S. Application Data

(60) Provisional application No. 61/163,501, filed on Mar. 26, 2009.

(51) Int. Cl.
*G01T 1/00* (2006.01)
(52) U.S. Cl.
USPC ............ 250/393; 250/363.01; 250/366
(58) Field of Classification Search
USPC ............ 250/363.01–363.09, 363.1, 393; 327/101; 341/155, 162; 378/19
See application file for complete search history.

(56) References Cited

U.S. PATENT DOCUMENTS

| 4,052,620 | A | * | 10/1977 | Brunnett ........................ 378/97 |
| 4,109,168 | A | * | 8/1978 | Raymond ..................... 327/101 |
| 4,170,733 | A | | 10/1979 | Weiss |
| 4,991,111 | A | | 2/1991 | Crookshanks |
| 5,113,077 | A | | 5/1992 | Shimizu et al. |
| 5,813,983 | A | | 9/1998 | DiFilippo et al. |
| 5,892,585 | A | * | 4/1999 | Lianza et al. ................. 356/405 |
| 6,510,195 | B1 | | 1/2003 | Chappo et al. |
| 6,586,743 | B1 | * | 7/2003 | Overdick et al. ........ 250/370.11 |
| 6,671,345 | B2 | | 12/2003 | Vrettos et al. |
| 6,737,627 | B2 | | 5/2004 | Moses et al. |

(Continued)

FOREIGN PATENT DOCUMENTS

| JP | 11072565 | A | 3/1999 |
| JP | 2007187682 | A | 7/2007 |
| WO | 2008078231 | A1 | 7/2008 |

OTHER PUBLICATIONS

Luhta, R., et al.; A new 2D-tiled detector for multislice CT; 2006; SPIE, Medical Imaging; vol. 6142:61420U-2-61420U-4.

(Continued)

*Primary Examiner* — David Porta
*Assistant Examiner* — Taeho Jo

(57) ABSTRACT

A detector array (110) of an imaging system (100) includes a radiation sensitive detector (114, 116) that detects radiation and generates a signal indicative thereof. A current-to-frequency (I/F) converter (202) converts the signal to a pulse train having a frequency indicative of the signal for an integration period. Circuitry (120) generates a first moment and at least one higher order moment based on the pulse train.

20 Claims, 6 Drawing Sheets

(56) References Cited

U.S. PATENT DOCUMENTS

| | | | |
|---|---|---|---|
| 2002/0141530 A1* | 10/2002 | Vrettos et al. | 378/19 |
| 2002/0176067 A1* | 11/2002 | Charbon | 356/4.01 |
| 2004/0017224 A1 | 1/2004 | Tumer et al. | |
| 2005/0121617 A1* | 6/2005 | Heismann et al. | 250/370.11 |
| 2006/0119427 A1* | 6/2006 | Roos et al. | 330/86 |
| 2006/0281067 A1* | 12/2006 | Simpson et al. | 435/4 |
| 2008/0174464 A1* | 7/2008 | Robert | 341/155 |
| 2008/0217546 A1* | 9/2008 | Steadman et al. | 250/370.09 |
| 2009/0310003 A1* | 12/2009 | Collins | 348/308 |
| 2010/0226495 A1* | 9/2010 | Kelly et al. | 380/30 |

OTHER PUBLICATIONS

Whiting, B. R., et al.; Properties of preprocessed sinogram data in x-ray computed tomography; 2006; Med. Phys.; 33(9)3290-3303.

Whiting, B. R., et al.; Image quantization: statistics and modeling; 1998; SPIE Conference Medical Imaging; vol. 3336:261-262.

Pontes, E. W., et al.; Using Cumulants and Spectra to Model Nuclear Radiation Detectors; 2006; IEEE Trans. on Nuclear Science; 53(3)1292-1298.

Roessl, E., et al.; K-edge imaging in x-ray computed tomography using multi-bin photon counting detectors; 2007; Phys. Med. Biol.; 52:4679-4696.

\* cited by examiner

SPECTRAL IMAGING

CROSS REFERENCE TO RELATED APPLICATIONS

This application claims the benefit of U.S. provisional application Ser. No. 61/163,501 filed Mar. 26, 2009, which is incorporated herein by reference.

The following generally relates to spectral imaging and finds particular application to spectral computed tomography (CT). However, it is also amenable to other medical and non-medical applications.

An integrating computed tomography (CT) scanner generally includes an x-ray tube mounted on a rotatable gantry opposite a detector array. The x-ray tube rotates around an examination region and emits polychromatic radiation that traverses the examination region, and the detector array receives the radiation that traverses the examination region. The detector array includes a scintillator array optically coupled to a photosensor array, which is electrically coupled to detector electronics. The scintillator array absorbs radiation and produces light indicative thereof, the photosensor array converts the light into an electrical signal indicative thereof, and the electronics integrates the electrical signal, producing a signal indicative of a mean or average intensity value for each integration period. The resulting signal is reconstructed to generate volumetric image data, which can be processed to generate an image of a scanned subject or object. The resulting image includes pixels that typically are represented in terms of gray scale values corresponding to relative radiodensity. Such information reflects the attenuation characteristics of the scanned subject or object.

Various techniques have been proposed for deriving spectral information from an integrated signal. For example, one technique includes stacking rows of scintillator pixels on top of each other in the direction of the incoming radiation and providing respective photosensor pixels for each row. Generally, the lower energy photons are absorbed in the rows closer to the incoming radiation and the higher energy photons are absorbed in the rows farther from the incoming radiation. In another example, the tube voltage is switched between different voltages, providing one set of measurements for the lower tube voltage and another set of measurements for the higher tube voltage. In yet another instance, an imaging system is configured with multiple x-ray tubes, each being driven with a different tube voltage and, thus, multiple sets of measurements for different emission spectra are obtained. Unfortunately, the above-noted techniques may add specialized hardware and/or complexity, and/or increase overall system cost.

Aspects of the present application address the above-referenced matters and others.

In accordance with one aspect, a detector array of an imaging system includes a radiation sensitive detector that detects radiation and generates a signal indicative thereof. A current-to-frequency (I/F) converter converts the signal into a pulse train having a frequency indicative of the signal for an integration period. Circuitry generates a first moment and at least one higher order moment or higher order central moment based on the pulse train.

According to another aspect, a method includes detecting polychromatic radiation generated by a radiation source of an imaging system for an integration period, generating an electrical signal indicative of the detected radiation, generating a pulse train indicative of the electrical signal, and generating at least two moments for the integration period based on the pulse train.

According to another aspect, an imaging system includes a source that emits radiation that traverses an examination region and a detector array that detects radiation traversing an examination region. The detector array includes a radiation sensitive detector that receives the radiation and generates a signal indicative thereof. A current-to-frequency (I/F) converter converts the signal to a pulse train having a frequency indicative of the signal. Circuitry generates a first moment and at least one higher order moment based on the pulse train.

The invention may take form in various components and arrangements of components, and in various steps and arrangements of steps. The drawings are only for purposes of illustrating the preferred embodiments and are not to be construed as limiting the invention.

Figure 1:
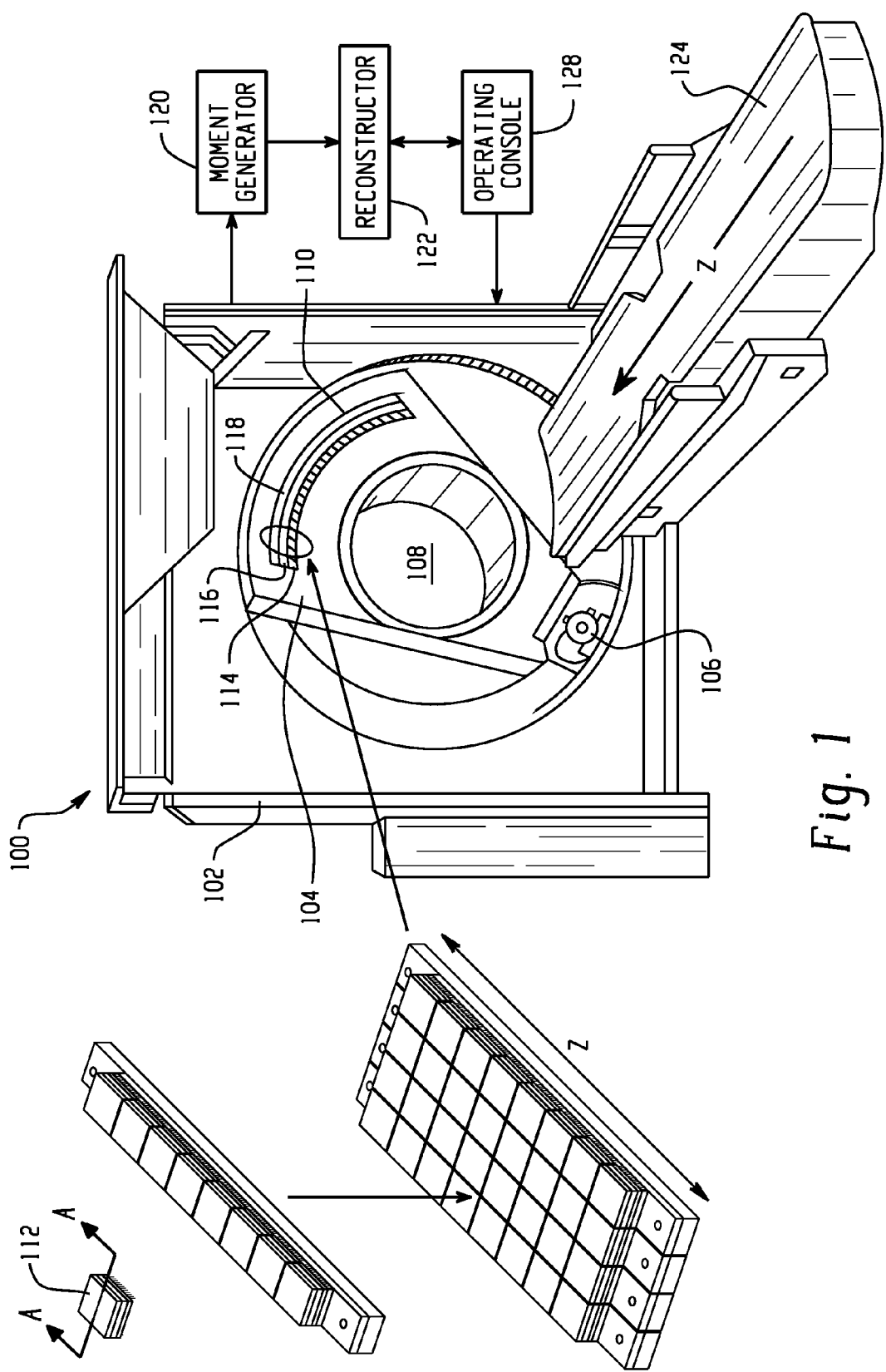
FIG. 1 illustrates an example imaging system.

FIG. 1 illustrates an imaging system 100 such as a computed tomography (CT) scanner. The system 100 includes a generally stationary gantry 102 and a rotating gantry 104. The rotating gantry 104 is rotatably supported by the generally stationary gantry 102. A radiation source 106, such as an x-ray tube, is supported by the rotating gantry 104 and rotates therewith around an examination region 108 about a longitudinal or z-axis, and emits polychromatic radiation. A source collimator or the like collimates radiation emitted by the radiation source 106, producing a generally cone, fan, wedge or otherwise-shaped radiation beam that traverse the examination region 108.

A detector array 110 subtends an angular arc opposite the examination region 108 relative to the radiation source 106. The detector array 110 receives radiation that traverses the examination region 108. The illustrated detector array 110 includes a two-dimensional array of detector mosaics or tiles 112. A non-limiting example of a such a detector array is described in U.S. Pat. No. 6,510,195B1, filed Jul. 18, 2001, and entitled "Solid State X-Radiation Detector Modules and Mosaics thereof, and an Imaging Method and Apparatus Employing the Same," which is incorporated herein by reference in its entirety.

The detector array 110 includes a radiation sensitive detector such as a detector tile 112 having a scintillator array 114 optically coupled to a photosensor array 116 (as illustrated) or a direction conversion material such as a CZT, CdTe, or other direct conversion material. The scintillator array 114 receives the radiation and produces light indicative thereof. The photo sensor array 116 receives the light and generates a signal such as an electrical current or voltage indicative thereof. Detector electronics 118 process the signal and generate data indicative thereof. An example of a suitable detector tile 112 is described in "A New 2D-Tiled Detector for Multislice CT," Luhta et al., Medical Imaging 2006: Physics of Medical Imaging, Vol. 6142, pp. 275-286 (2006).

In the illustrated embodiment, and as described in greater detail below, the detector electronics 118 include a current-to-frequency (or voltage-to-frequency) converter that integrate the signal output by the photosensor array 116 during an integration period and generates digital data, such as a pulse train having a frequency indicative of the signal, for the integration period. An example of a suitable converter is described in U.S. Pat. No. 6,671,345B2, filed Nov. 7, 2001, and entitled "Data Acquisition for Computed Tomography," which is incorporated herein by reference in its entirety. Another suitable converter is described in U.S. Pat. No. 4,052, 620, filed Nov. 28, 1975, and entitled "Data Acquisition for Computed Tomography," which is incorporated herein by reference in its entirety.

Circuitry or a moment generator 120 generates one or more moments (e.g., 1st moment, 2nd moment, 3rd moment, . . . , n-th moment) based on the digital signal from the current-to-frequency converter. Generating at least two moments allows for obtaining spectral information from the integrated signal. The moment generator 120 may be part of the detector electronics 118 on a tile 112, electronics remote from the tile 112, or a combination of electronics partially integrated with the detector electronics 118 on the tile 112 and partially remote from the tile 112.

A reconstructor 122 reconstructs the output of the moment generator 120. In one instance, the reconstructor 122 individually reconstructs at least two moments using a conventional reconstruction algorithm. The resulting volumetric image data can then be used to obtain additional spectral information on a pixel-by-pixel basis from the effective absorption at different energy moments. In another instance, the reconstructor 122 reconstructs the moments based on a spectral reconstruction algorithm. For example, the reconstruction algorithm may include decomposing the signals to obtain various absorption components in the signals, such as a photo electric component, a Compton component, one or more K-edges, etc. The component signals can then be used in conventional reconstruction algorithms to generate component images showing the density distribution of the components.

A couch or patient support 124 supports a subject, such as a human or animal, or an object within the examination region 108. The support 124 is movable, which enables an operator or the system to suitably position the subject within the examination region 108 before, during and/or after scanning. A computing system such as an operator console 128 facilitates user interaction with the scanner 100. Software applications executed by the operator console 128 allow the user to configure and/or control operation of the scanner 100. For instance, the user can interact with the operator console 128 to select a spectral or conventional imaging protocol.

As noted above, in the illustrated embodiment a current-to-frequency (I/F) converter integrates the photosensor array 116 output signal during an integration period and generates digital data such as a pulse train having a frequency indicative of the signal for the integration period. The output signal of the photosensor array 116 can be represented as E(t), and the output of the I/F converter, from a first pulse N0 at time $T_{N0}$ to a last N1 pulse at time $T_{N1}$ of an integration period T, can be represented as a function of Equation 1:

$$\int_{T_{N0}}^{T_{N1}} E(t)dt, \quad \text{Equation 1}$$

or in discrete form as shown in Equation 2:

$$\frac{NQ_p}{T_{N1} - T_{N0}}, \text{ or } \frac{NQ_p}{\Delta T} \quad \text{Equation 2}$$

wherein N represents the number of pulses in the interval from $T_{N0}$ to $T_{N1}$, excluding the very first pulse, $Q_p$ represents a predetermined constant charge value between adjacent pulses, and $\Delta T = T_{N1} - T_{N0}$. Equation 2 can be used as an estimate of the input signal E(t) and represents the mean value $\bar{I}$ or the first moment, of E(t).

The variations between the individual pulses in a pulse train can be used to estimate higher moments, as discussed next. The n-th moment can be determined based on Equation 3:

$$\int_{T_{N0}}^{T_{N1}} (E(t))^n dt, \quad \text{Equation 3}$$

A pulse is generated during the integration period if the equality of Equation 4 is satisfied:

$$\int_{t_i}^{t_{i+1}} E(t)dt = Q_p, \quad \text{Equation 4}$$

wherein the interval from $t_i$ to $t_{i+1}$ represents the time interval between adjacent pulses in the integration period. E(t), for the interval from $t_i$ to $t_{i+1}$, can be approximated as a function of Equation 5:

$$\frac{Q_p}{t_{i+1} - t_i}, \text{ or } \frac{Q_p}{\Delta t_i}. \quad \text{Equation 5}$$

Substituting Equation 5 into Equation 3 renders Equation 6:

$$\int_{T_{N0}}^{T_{N1}} \left(\frac{Q_p}{t_{i+1} - t_i}\right)^n dt. \quad \text{Equation 6}$$

or in discrete form as Equation 7:

$$\sum_{i=N0}^{N1-1} \left(\frac{Q_p}{t_{i+1} - t_i}\right)^n (t_{i+1} - t_i), \quad \text{Equation 7}$$

or as Equation 8:

$$Q_p^n \sum_{i=N0}^{N1-1} \frac{1}{(t_{i+1} - t_i)^{n-1}}, \quad \text{Equation 8}$$

Equations 7 and 8 provide an estimate of the n-th moment over the interval from $T_{N0}$ to $T_{N1}$.

Figure 2:
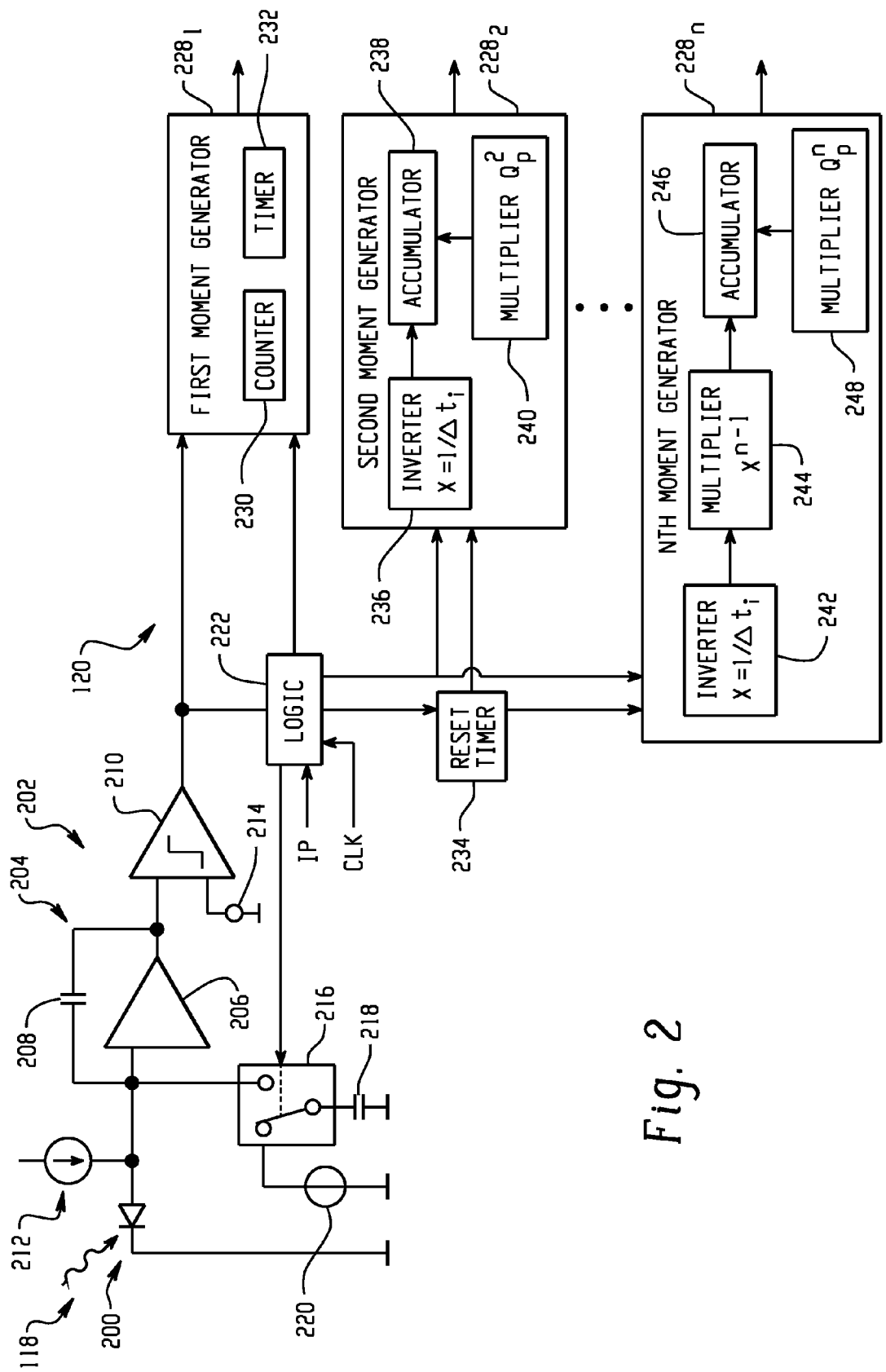
FIGS. 2 and 3 illustrate example processing electronics.

FIG. 2 illustrates a non-limiting embodiment of a photosensor pixel 200 of the photosensor array 116, the detector electronics 118 and the moment generator 120 when configured to generate moments based on the Equations 2 and 8. An analog-to-digital (A/D) converter 202 includes an integrator 204 (an amplifier 206 and an integrating capacitor 208) and a discriminator or comparator 210. As noted above, the illustrated A/D converter 202 is employed as a current-to-frequency (I/F) converter.

The integrator 204 integrates a summation of the signal (E(t)) output by the photosensor pixel 200 and a bias current 212 during an integration period. In one instance, the bias current 212 is set so that the analog-to-digital converter 202 produces a predetermined number of pulses over a predetermined number of integration periods such as at least one pulse over three integration periods, at least two pulses per integration, etc. The comparator 210 compares the output of the integrator 204 with a threshold 214 during the integration period and generates a digital pulse when the output of the integrator 204 meets the threshold 214.

A reset switch 216 is used to reset the integrator 204 during the integration period in response to the generation of a digital pulse. The reset switch 216 may also be used to reset the integrator 204 between integration periods. Resting the integrator 204 may include injecting charge stored in a capacitor 218 into the input of the integrator 204 to cancel the charge at the input of the integrator 204. When open, the switch 216 electrically connects the reset capacitor 218 with a reference voltage 220. Logic 222 controls the reset switch 216, including closing the reset switch 216 to reset the integrator 204 in response to detecting a pulse in the comparator output, on an integration period boundary, and/or otherwise.

A first moment generator $228_1$ generates the mean value $\bar{I}$ for example, via Equation 2, which, as discussed above, provides an estimate of the input signal E(t). In one instance, a counter 230 counts the number of pulses output by the comparator 210 for an integration period and a timer 232 determines a time between a first pulse to a last pulse of the integration period. From this data, the first moment generator $228_1$ generates the first moment, for example as a function of a ratio of the pulse count to the time between the first and last pulses.

A second moment generator $228_2$ generates the second moment, for example, based on Equation 8. A reset timer 234 is used to determine the time between adjacent pulses ($\Delta t_i$) during an integration period for a plurality of pulses of the pulse train. An inverter 236 inverts the time value between the adjacent pulse, and an accumulator 238 accumulates the inverted data. The reset timer 234 determines a new time value for each pair of adjacent pulses, and the accumulator 238 accumulate inverted data in response to the generation of each pulse. As such, the second moment is incrementally generated with the generation of each pulse during an integration period. A multiplier 240 multiplies the accumulated time by the constant charge value raised to the second power ($Q_p^2$). The accumulator 238 is initially invoked to accumulate the output of the multiplier 240 in response to generation of a first pulse during an integration period, and cleared or rest at the end of the integration period after the accumulated data is read out. The reset timer 234 is reset in response to the generation of a pulse.

An n-th moment generator $228_n$ generates an n-th moment, for example, based on Equation 8. Again, the reset timer 234 is used to determine the time between adjacent pulses. An inverter 242 inverts the time value, and a multiplier 244 multiplies the inverted value by itself n−1 times, or raises the inverter value to the (n−1)-th power. An accumulator 246 accumulates this data for the integration period. A multiplier 248 multiplies the accumulated time the constant charge value raised to the n-th power ($Q_p^n$). Likewise, the accumulator 246 is invoked to accumulate in response to the generation of a first pulse in the integration period and is cleared or reset at the end of the integration period after the accumulated data is read out, and the reset timer 234 is reset in response to the generation of a pulse. The nth moment generator $228_n$ can alternatively or additionally be used to generate the first and/or second moments, as well as one or more higher moments.

In the illustrated embodiment, the logic 222 resets the reset timer 234 and invokes and clears the accumulators 238 and 246. In other embodiment, the reset timer 234 is otherwise reset and/or the accumulators 238 and 246 are otherwise invoked and/or cleared. In addition, a sub-portion or all of the components of the moment generator 120 can be integrated with the detector electronics 118 on the tile 112 or can be located remote from the tile 112. The generated moments are conveyed to the reconstructor 122, which reconstructs the moments individually and/or in combination as described above.

The following describes another non-limiting technique for generating one or more moments. With this example, central moments are employed to determine higher order moments. As noted above, the mean $\bar{I}$ of the current signal E(t), which the photodiode generates from the light generated in the scintillator can be estimated as a function of Equation 2. The mean $\bar{I}$ can also expressed as shown in Equation 9:

$$\frac{NQ_p}{\sum_{i=N0}^{N1-1} \Delta t_i}, \qquad \text{Equation 9}$$

wherein $\Delta t_i$ represents the time intervals between adjacent pulses, and N=N1−N0 corresponds to the number of all pulses in the measurement interval excluding the very first pulse. The n-th central moment of the current signal can be estimated as a function of Equation 10 (which represents the discretized version of the definition of the n-th central moment):

$$\frac{1}{\sum_{i=N0}^{N1-1} \Delta t_i} \sum_{i=N0}^{N1-1} (I_i - \bar{I})^n \Delta t_i, \qquad \text{Equation 10}$$

wherein $I_i$ is a function of Equation 11:

$$I_i = Q_p/\Delta t_i. \qquad \text{Equation 11}$$

Substituting Equation 11 in Equation 10 and expressing $\bar{I}$ as shown in Equation 12:

$$\bar{I} = \frac{1}{\sum_{i=N0}^{N1-1} \Delta t_i} \sum_{l=N0}^{N1-1} I_l \Delta t_l = \frac{NQ_p}{\sum_{i=N0}^{N1-1} \Delta t_i}, \qquad \text{Equation 12}$$

results in Equation 13:

$$\frac{Q_p^n}{\sum_{i=N0}^{N1-1} \Delta t_i} \sum_{i=N0}^{N1-1} \left( \frac{1}{\Delta t_i} - \frac{N}{\sum_{l=N0}^{N1-1} \Delta t_l} \right)^n \Delta t_i, \qquad \text{Equation 13}$$

which can, for n=2, also be expressed as Equation 14 (observing that for a random signal I(t) the $2^{nd}$ order central moment is given by $\overline{\sigma_I^2(t)} = E[(I-E[I])^2] = E[I^2] - E^2[I]$, where $E[\blacksquare]$ denotes the expectation value or mean value):

$$\frac{Q_p^2}{\sum_{i=N0}^{N1-1} \Delta t_i} \left( \sum_{i=N0}^{N1-1} \left( \frac{1}{\Delta t_i} \right) - N \left( \frac{N}{\sum_{i=N0}^{N1-1} \Delta t_i} \right) \right), \qquad \text{Equation 14}$$

where $\bar{I}$ is again expressed as shown in Equation 12, and $\overline{I^n}$ (for n=2) is expressed as shown in Equation 15:

$$\overline{I^n} = \frac{1}{\sum_{i=N0}^{N1-1} \Delta t_i} \sum_{l=N0}^{N1-1} I_l^n \Delta t_l = \frac{Q_p^n}{\sum_{i=N0}^{N1-1} \Delta t_i} \sum_{l=N0}^{N1-1} \left(\frac{1}{\Delta t_l}\right)^{n-1}. \quad \text{Equation 15}$$

For n>2, the general relationships between the central moment $M_n = E[I - E[I^n]]^n]$ and the "moment about the origin" $M_n^* = E[I^n]$ have to be observed, e.g. $M_3 = M_3^* - 3M_1^* M_2^* + 2[M_1^*]^3$ for n=3. The general rule is:

$$M_n = \sum_{j=0}^{n} \binom{n}{j} M_{n-j}^* (-M_1^*)^j,$$

where $M_0^* := 1$, and $M_1^* = E[I]$ is the ordinary mean value.

Figure 3:
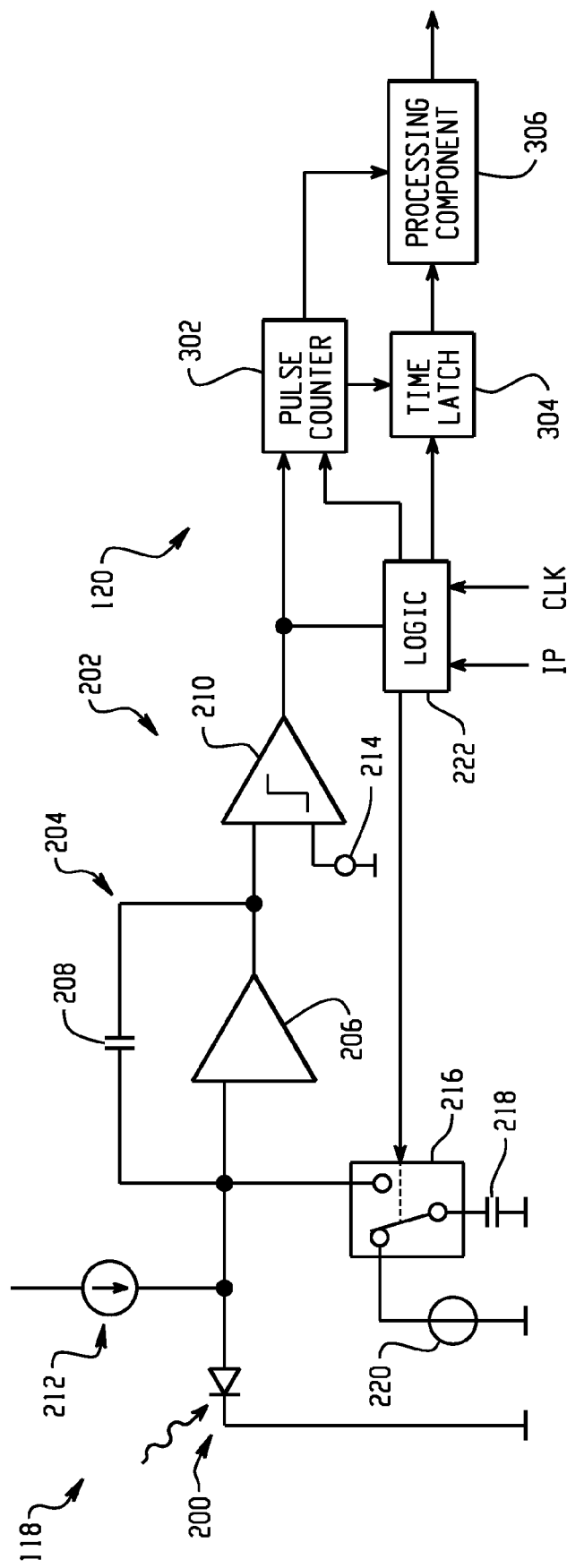

FIG. 3 illustrates a non-limiting embodiment of the photosensor pixel 200, the detector electronics 118 and the moment generator 120 when configured to generate moments based on the Equations 2 and 13 or 14. As discussed above, the analog-to-digital (A/D) converter 202, which is configured as a current-to-frequency (I/F) converter, includes the integrator 204 (the amplifier 206 and the integrating capacitor 208) and the comparator 210. The integrator 204 integrates a summation of the signal output by the photosensor pixel 200 and the bias current 212 during an integration period, and the comparator 210 generates a digital pulse when the output of the integrator 204 meets the threshold 214. The logic 222 controls the reset switch 216, which resets the integrator 204 for an integration period and in response to the generation of a digital pulse during the integration period.

In this embodiment, the moment generator 120 includes a pulse counter 302 that counts the pulses in the output of the comparator 210 during an integration period. The moment generator 120 also includes a time latch 304 that latches the time instances of the pulses during the integration period. In one non-limiting instance, the time latch 304 includes a register or the like with as many memory cells as there are clock ticks in the integration period. With this configuration, the cells are set to an initial known state (e.g., "0"), and the logic 222 writes a known value (e.g., "1") to a cell if a pulse is generated with the corresponding clock tick. The distance in cell position of cells storing a logical "1" provides information that can be used to derive the time distance, in clock ticks, between adjacent pulses. Other embodiments of the time latch 304 are also contemplated herein. The logic 222 invokes read out of the pulse count and time instances and resets or clears the pulse counter 302 and/or the time latch 304.

A processing component 306 generates one or more moments, such as at least two moments, based on the output of the pulse counter 302 and the output of the time latch 304 based on Equation 13 or 14.

For the embodiments herein and variations thereof, a sampling rate of the converter 202 can be determined based on a highest moment to be generated. By way of non-limiting example, the sampling rate for determining a suitable estimate of $\overline{I^n}$ generally is higher than for determining a suitable estimate of $\bar{I}$. For instance, the Fourier transform (F{ }) of $I^n(t)$ is n-fold convolution of F{I(t)}. As an approximation, the sampling rate for determining higher order moments can be increased by a factor of n, relative to n=1, since the bandwidth of $F\{I^n(t)\}$ is approximately n times the bandwidth of $F\{I(t)\}$. The sampling rate can be adjusted through the threshold 214, with a smaller threshold resulting in a higher sampling rate relative to a higher threshold, and/or otherwise.

It is to be appreciated that the embodiments described herein can be used in connection with one or more other spectral imaging approaches. For instance, the embodiments described herein can be used in combination with a spectral detector (e.g. a dual-layer system), kVp switching, and/or a multi-tube system. By combining the embodiments described herein with one or more of the techniques and/or other techniques, the spectral separation resolution can be increased.

Figure 4:
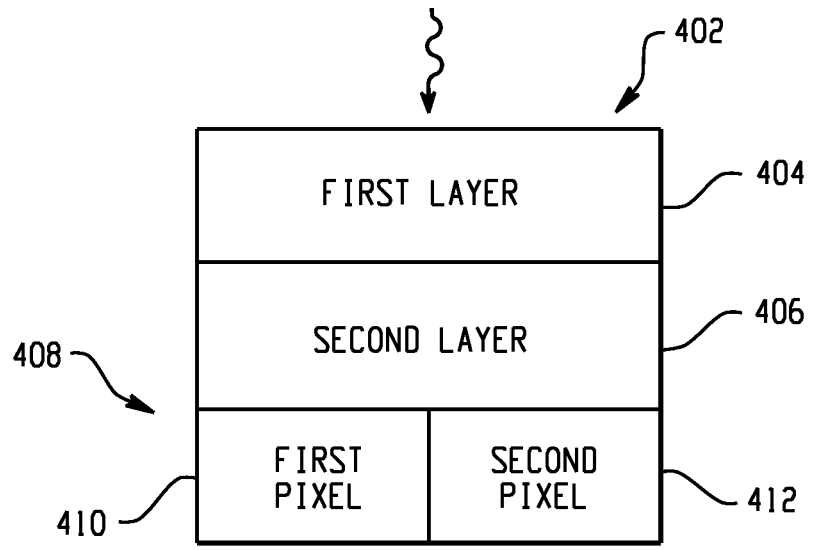
FIGS. 4 and 5 illustrate example spectral detectors.

An example of a spectral detector is shown in FIG. 4. A scintillator array 402 includes first and second layers of scintillator pixels 404, 406 are stacked in a direction of the incoming radiation. Absorption of the incoming radiation in the scintillator array 402 is energy-dependent, with lower energy photons travelling on average a shorter distance through the scintillator array 402 before being absorbed in the first layer 404, and higher energy photons travelling on average a greater distance through the scintillator array 402 before being absorbed in a second layer 406. As such, the depth of the absorption is indicative of the energy of the detected radiation. The scintillator array 402 is optically coupled on top of a photosensor array 408 having a first photosensitive pixel 410 with a first spectral response tuned to one of the first or second scintillator layers 404, 406 and a second photosensitive pixel 412 with a second spectral response tuned to the other of the first or second scintillator layers 404, 406. In this manner, the photosensor array 408 will have two spectrally different outputs.

Figure 5:
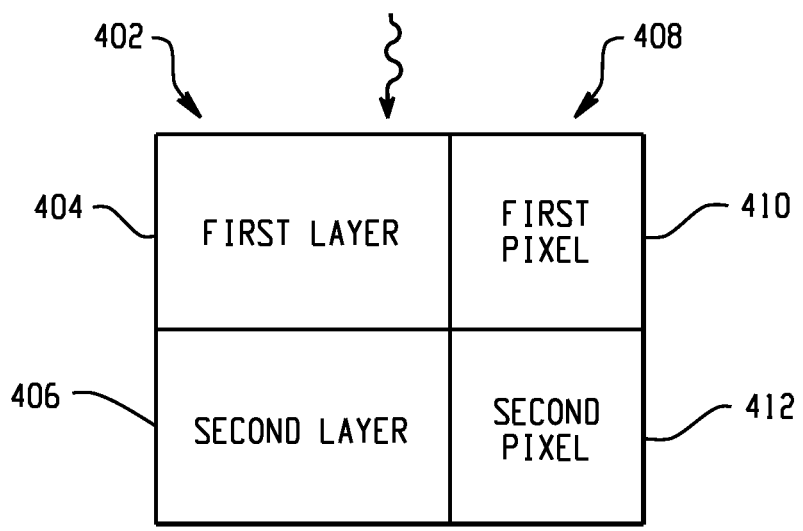

Another example of a spectral detector is shown in FIG. 5. In this example, the first and second scintillator pixels 404, 406 are respectively optically side-mounted to the photosensor array 408. Likewise, the photosensor array 408 will have two spectrally different outputs. A light reflective film or coatings can be placed on the sides of the scintillator pixels 404, 406 not coupled to the photosensor array 408 to direct light towards the photodiode array 408. With either or both FIGS. 4 and 5, it is to be appreciated that the scintillator pixels 404, 406 can be formed from the same or different emitter materials, and/or the scintillator pixels 404, 406 can have similar or different dimensions, such as similar or different depths in the direction of the incoming radiation. Of course, more scintillator layers and photosensitive pixels can be used in other embodiments.

Figure 6:
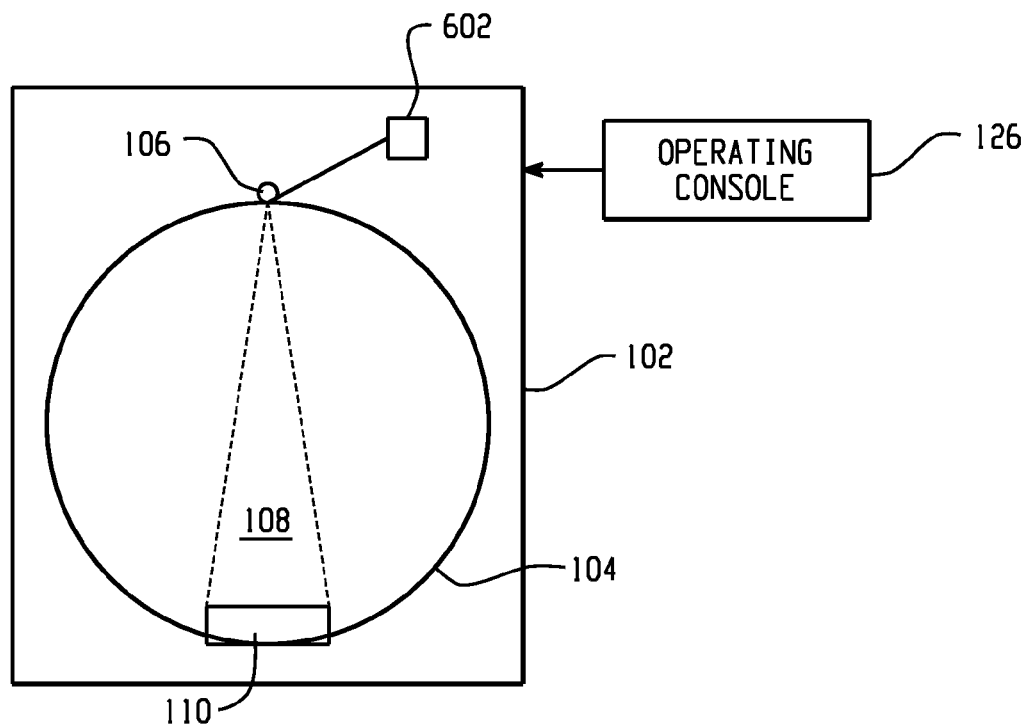
FIGS. 6 and 7 illustrate example multi-energy imaging systems.

FIG. 6 illustrates an example of kVp switching. In this example, an x-ray tube controller 602 switches the tube voltage between two (or more) different voltage levels. The controller 602 can switch the tube voltage during a scan (e.g., within a view, between views, etc.), between scans, and/or otherwise, for example, based on scanning information from the console 128. The detector array 110 will generate first signals corresponding to a first tube voltage and second signals corresponding to a second tube voltage.

Figure 7:
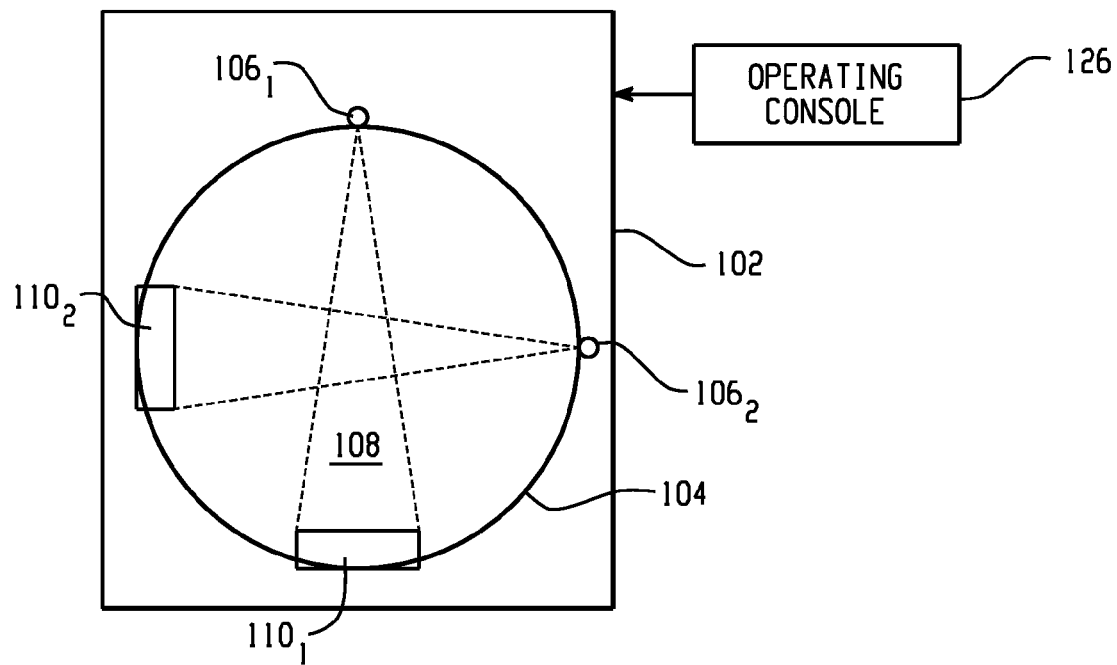

FIG. 7 illustrates an example a multi-tube system. For explanatory purposes, the system is shown with a first tube/detector pair $106_1/110_1$ and a second tube/detector pair $106_2/110_2$. In other embodiments, the system can be configured with more tube/detector pairs such a three or more tube/detector pairs. In this example, each tube $106_1/106_2$ is operated at a different tube voltage. As a result, each detector $110_1/110_2$ provides an output corresponding to different spectra.

In yet another instance, a spectral decomposition algorithm can be used to separate various components such the photoelectric effect component and the Compton effect component. A suitable decomposition is described in Roessl et al., "K-edge imaging in x-ray computed tomography using multi-bin photo counting detectors," Physics in Medicine and Biology, 2007, pages 4679-4696, vol. 52. Another suitable decomposition is described in application serial number PCT/IB2007/055105, filed on Dec. 14, 2007, and published as WO2008078231, which is incorporated herein by reference in its entirety. In the latter, the decomposition is extended to derive K-edge components for K-edge materials administered via contrast agents.

Exemplary applications in which the systems and methods described herein can be employed include, but are not limited to, baggage inspection, medical applications, animal imaging, heart scanning, material testing, non-destructive imaging, machine vision, and material science. In addition, applications apply to x-ray CT systems using multiple tubes (and multiple detectors) on a single CT gantry. Other suitable applications include applications where tissue differentiation through higher spectral performance plus the possibility to implement K-edge imaging in a CT system based on current-integrating detectors is desired.

Figure 8:
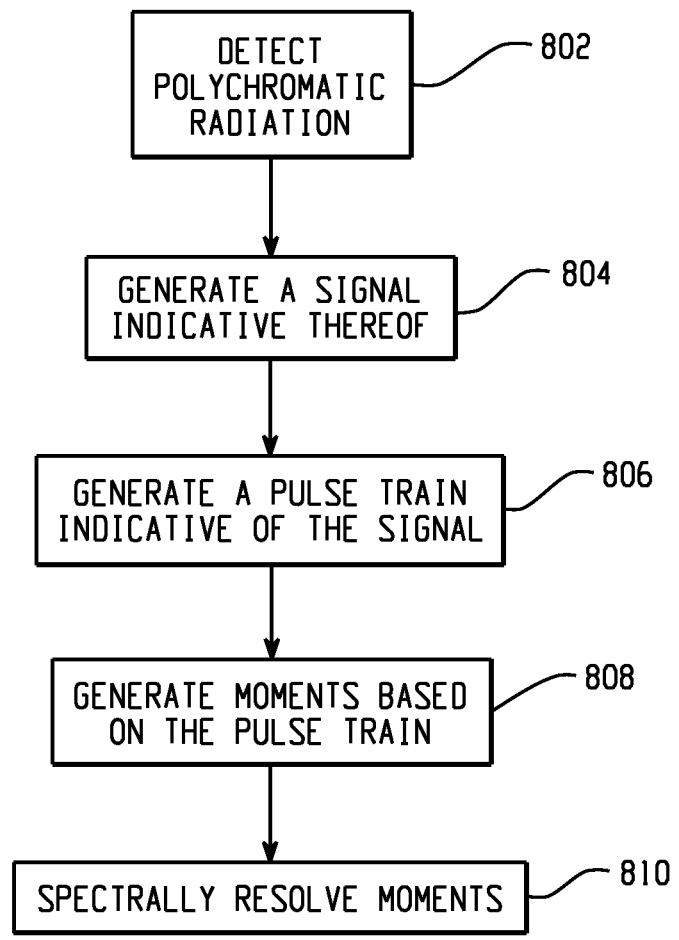
FIG. 8 illustrates an example method.

FIG. 8 illustrates a method.

At 802, polychromatic radiation traversing an examination region is detected.

At 804, a signal indicative of the detected radiation is generated.

At 806, a pulse train having a frequency indicative of the detected radiation is generated based on the signal.

At 808, one or more moments are generated based on the pulse train as described herein.

At 810, the moments are spectrally resolved in the projection and/or image domains.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

What is claimed is:

1. A detector array of an imaging system, comprising:
a radiation sensitive detector that detects radiation and generates a signal indicative thereof;
a current-to-frequency (I/F) converter that converts the signal into a pulse train having a frequency indicative of the signal for an integration period; and
circuitry that generates a first moment and at least one higher order moment based on the pulse train.

2. The detector array of claim 1, wherein the first and the at least one higher order moment correspond to different spectral information for polychromatic radiation illuminating the radiation sensitive detector.

3. The detector array of claim 1, wherein the first and the at least one higher order moment are spectrally resolved in a projection data or image data domain.

4. The detector array of claim 1, wherein the circuitry generates the at least one higher order moment during the integration period.

5. The detector array of claim 1, further including a reset timer that determines a time value between adjacent pulses in the pulse train, wherein the circuitry generates the at least one higher order moment based on the time between adjacent pulses.

6. The detector array of claim 5, further including:
an inverter that inverts the time value; and
an accumulator that accumulates a plurality of inverted time values corresponding to different pairs of pulses during the integration period, wherein the circuitry generates the at least one higher moment based on the accumulated inverted time values.

7. The detector array of claim 6, wherein the accumulator accumulates the inverted time value in response to generation of a pulse in the pulse train.

8. The detector array of claim 6, further including a multiplier that multiples the accumulated time values by a predetermined charge value.

9. The detector array of claim 6, further including a second multiplier that multiples the inverted time value, prior to being accumulated, by itself n−1 times, wherein n corresponds to a degree of the higher order moment.

10. The detector array of claim 1, further including a time latch that latches time data for pulses in the pulse train.

11. The detector array of claim 10, wherein the time data includes time differences between adjacent pulses in the pulse train.

12. The detector array of claim 10, further including a processing component that generates the first and the at least one higher order moment based on a pulse count of the pulses in the pulse train and the time data.

13. A method, comprising:
detecting polychromatic radiation generated by a radiation source of an imaging system for an integration period;
generating an electrical signal indicative of the detected radiation;
generating a pulse train indicative of the electrical signal; and
generating at least two different moments for the integration period based on the pulse train.

14. The method of claim 13, wherein the at least two moments correspond to different spectral information about the detected polychromatic radiation.

15. The method of claim 13, further including spectrally resolving the at least two moments.

16. The method of claim 13, further including determining time differences between adjacent pulses in the pulse train, and wherein generating the at least two moments includes generating the at least two moments based on the time differences.

17. The method of claim 16, further comprising generating the at least two moments during the integration period as time differences are determined.

18. The method of claim 16, further comprising generating the at least two moments upon conclusion of the integration period.

19. The method of claim 13, further comprising reconstructing the at least two moments to generate volumetric image data.

20. An imaging system, comprising:
a source that emits radiation that traverses an examination region; and
a detector array that detects radiation traversing an examination region, the detector array, comprising:
a radiation sensitive detector that receives the radiation and generates a signal indicative thereof;
a current-to-frequency (I/F) converter that converts the signal into a pulse train having a frequency indicative of the signal; and
circuitry that generates a first moment and at least one higher order moment based on the pulse train.

* * * * *